(12) United States Patent
Xie et al.

(10) Patent No.: US 11,731,950 B2
(45) Date of Patent: Aug. 22, 2023

(54) MASS PRODUCTION AND APPLICATION OF Δ 8 THC

(71) Applicant: Shuang Xie, Vancouver (CA)

(72) Inventors: Shuang Xie, Vancouver (CA); Betty Cai, Vancouver (CA); Allen Xie, Vancouver (CA)

( * ) Notice: Subject to any disclaimer, the term of this patent is extended or adjusted under 35 U.S.C. 154(b) by 148 days.

(21) Appl. No.: 17/447,019

(22) Filed: Sep. 7, 2021

(65) Prior Publication Data

US 2022/0073489 A1     Mar. 10, 2022

Related U.S. Application Data

(60) Provisional application No. 63/086,076, filed on Oct. 1, 2020, provisional application No. 63/075,261, filed on Sep. 7, 2020.

(51) Int. Cl.

| | | |
|---|---|---|
| *C07D 311/80* | (2006.01) | |
| *A61K 36/82* | (2006.01) | |
| *A61K 31/352* | (2006.01) | |
| *A61K 36/185* | (2006.01) | |
| *A61K 9/00* | (2006.01) | |
| *B01D 3/12* | (2006.01) | |
| *B01D 3/10* | (2006.01) | |
| *B01D 1/22* | (2006.01) | |
| *A23L 33/105* | (2016.01) | |
| *A23L 2/52* | (2006.01) | |
| *A24B 15/167* | (2020.01) | |

(52) U.S. Cl.
CPC .............. *C07D 311/80* (2013.01); *A23L 2/52* (2013.01); *A23L 33/105* (2016.08); *A24B 15/167* (2016.11); *A61K 9/0095* (2013.01); *A61K 31/352* (2013.01); *A61K 36/185* (2013.01); *A61K 36/82* (2013.01); *B01D 1/222* (2013.01); *B01D 3/10* (2013.01); *B01D 3/12* (2013.01); *A23V 2002/00* (2013.01)

(58) Field of Classification Search
None
See application file for complete search history.

(56) References Cited

FOREIGN PATENT DOCUMENTS

WO    WO 2015068052 A2 *   5/2015

\* cited by examiner

*Primary Examiner* — Michael V Meller
(74) *Attorney, Agent, or Firm* — Syncoda LLC; Feng Ma

(57) ABSTRACT

A process of converting cannabidiol (CBD) to $\Delta^8$-tetrahydrocannabinol ($\Delta^8$-THC) or $\Delta^9$-tetrahydrocannabinol ($\Delta^9$-THC) can enable mass production of $\Delta^8$-THC and/or $\Delta^9$-THC, achieve greater yields and higher purity in comparison to previously reported processes while eliminating the use of organic solvent. The resultant hemp-derived $\Delta^8$-THC can be mixed with and absorbed by natural extracts, including tea extract, starch, sugar, lecithin, and other emulsifiers. $\Delta^8$-THC used in edible, topical and vaping products such as powdered $\Delta^8$-THC food ingredients, tablets or pills, suppositories, and vape formulations are disclosed. Further described are beverages and baked goods utilizing or incorporating the tablets or powdered $\Delta^8$-THC to create edible products containing an emulsified, tasteless, and odorless dose of $\Delta^8$-THC. The disclosure also describes a rectal suppository designed to provide improved comfort of use. A $\Delta^8$-THC liquid composition can be use in an electronic cigarette smoking device for pulmonary administration of $\Delta^8$-THC, which results in more effective absorption.

1 Claim, 3 Drawing Sheets

Δ⁸-tetrahydrocannabinol (Δ⁸-THC)

Δ⁹-tetrahydrocannabinol (Δ⁹-THC)

Cannabidiol (CBD)

MASS PRODUCTION AND APPLICATION OF Δ 8 THC

CROSS-REFERENCE TO RELATED APPLICATIONS

This application claims priorities under 35 U.S.C. 119(e) to U.S. Provisional Patent Application Ser. Nos. 63/086,076 filed on Oct. 1, 2020, and 63/075,261 filed on Sep. 7, 2020, the disclosures of which are hereby incorporated by reference in their entirety.

BACKGROUND

Recent developments in medical science have propelled growing interest in the medicinal effects and uses of *cannabis*, which produces a group of chemicals called cannabinoids. There is a growing base of evidence on the various medicinal effects and uses of *cannabis*, which produces a group of chemicals called cannabinoids.

SUMMARY

This disclosure relates to mass production methods for the isomerization of cannabidiol and relate generally to methods and compositions of matter which enable concentrated $\Delta^8$-THC distillate to be stable, emulsifiable, and flavorless for use in food, beverages, vape juice, and suppositories. Embodiments of the disclosure also relate to a variety of culinary uses for the stabilized, emulsified, and concentrated $\Delta^8$-THC distillate and a liquid composition comprising of naturally or artificially derived $\Delta^8$-THC, emulsifiers, and flavoring agents, to be smoked using a smoking device such as an electronic cigarette (e-cigarette).

Figure 1:
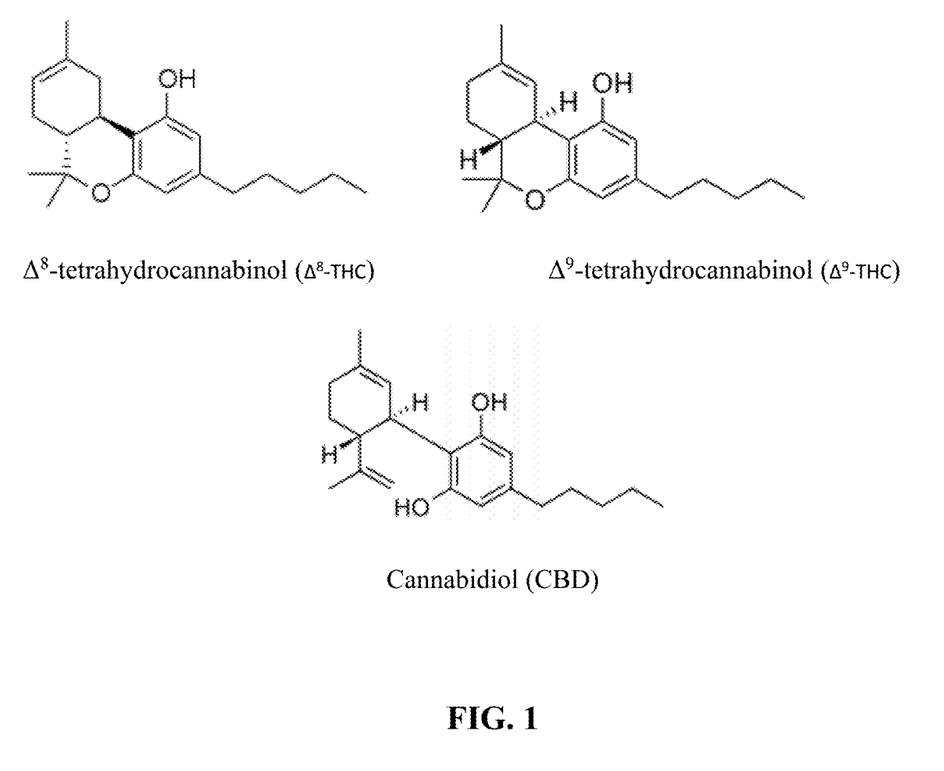
FIG. 1 illustrates chemical structures of cannabinoid compounds.
Figure 2:
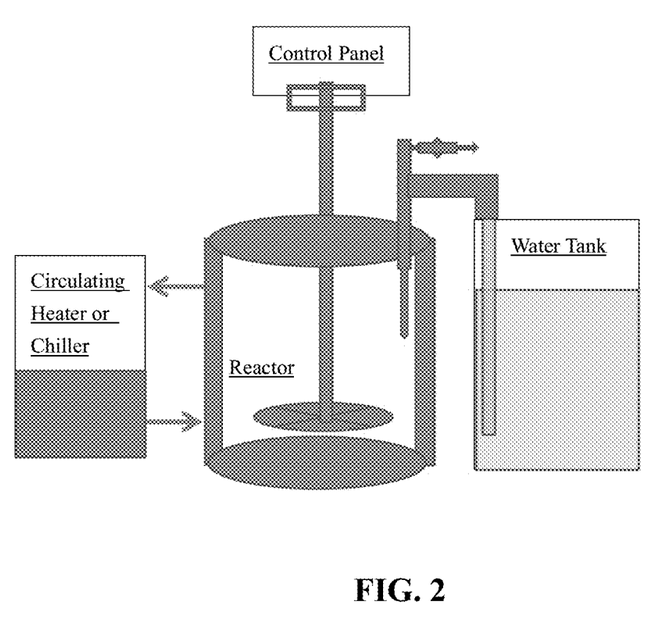
FIG. 2 illustrates a schematic diagram of a conversion reactor apparatus.
Figure 3:
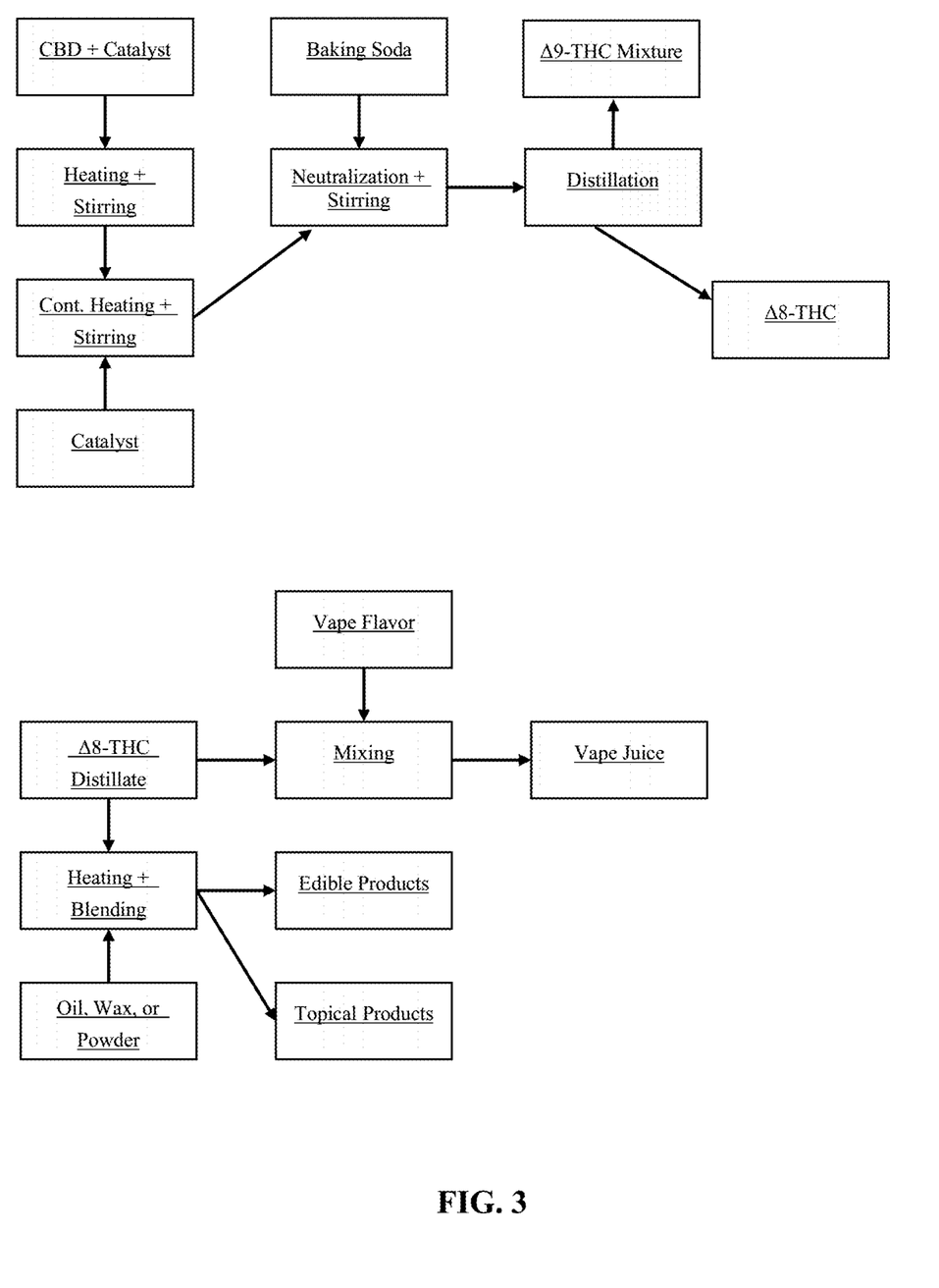
FIG. 3 schematically illustrates a conversion process (top panel) and an application (bottom panel).

Various embodiments of this disclosure provide a novel method to convert cannabidiol (CBD) to tetrahydrocannabinol (THC). The reaction is proceeded without any organic solvent via the following process:

Providing a reactor that contains a mixer and heater without organic solvent. The reactor is connected to a water buffer tank through a tube or pipe (FIG. 2);

Adding cannabidiol and acid or catalyst to the reactor;

Mixing and heating the reaction mixture;

Turning off the heater and cooling the mixture to room temperature;

Going to step 34 if specific reaction mixture of desired $\Delta^8$-THC-to-$\Delta^9$-THC ratio is achieved;

Adding the second catalyst to the reactor to achieve complete conversion to $\Delta^8$-THC; and Starting the heater and mixer;

Turning off the heater when conversion is finished;

Adding neutralizing agent such as baking soda to the mixture; and

Distilling the mixture and keep the light portion of the distillate to yield $\Delta^8$-THC and/or $\Delta^9$-THC distillate Embodiments of the present disclosure address the needs described above and relate to making concentrated $\Delta^8$-THC distillate stable, emulsifiable, and flavorless through the addition of a tea extract powder and/or other commonly used ingredients and subsequent mixing with emulsifier powder. This concentrated $\Delta^8$-THC distillate-infused powder is effective as a food and beverage additive.

Another objective of the present disclosure is to provide an edible powdered *cannabis* concentrate that is suitable for use via sub-lingual ingestion.

Another objective of the present disclosure is to provide a composition that serves as an easy and accurate means to control dosage amounts of cannabinoid concentrates and extracts for the treatment of medical conditions and symptoms.

An objective and advantage of the present disclosure is to provide a standardized and measurable dosage of $\Delta^8$-THC in powder, capsule, or tablet form, thus enabling patients to accurately and repeatably deliver the same dose to address their medical needs.

Another objective and advantage of the present disclosure is to provide a few convenient ways to consume $\Delta^8$-THC and cannabinoids.

Another embodiment of the disclosure is a rectal suppository comprising $\Delta^8$-THC or other cannabinoid concentrates and one or more pharmaceutically acceptable excipients, wherein the total weight of the suppository ranges from about 500 mg to about 3000 mg.

The $\Delta^8$-THC distillate powder of the present disclosure is effective for use in beverages such as coffees and teas, in bottled beverages, in food or beverage additive packets intended to be poured directly into hot beverages, including tea bags, coffee pods/filters, infusion blends/packets such as fruit infusions, ground coffee and instant coffee powders, as well as in recipes for baked goods or hot foods. Additionally, the $\Delta^8$-THC distillate powder of the present disclosure lends itself to encapsulation and can be ingested orally in either tablet or powder form.

The present disclosure also relates to methods to make the smoke-able $\Delta^8$-THC composition which utilize a mixture composition of $\Delta^8$-THC with emulsifiers and/or flavor enhancers to form a composition to be smoked in an electronic cigarette. The present disclosure finally relates to a smoking device containing a smoke-able $\Delta^8$-THC composition.

In another aspect, a method for pulmonary administration of a Δ8-THC composition to a mammal is provided, the method including:

providing a smoke-able composition comprising:

Δ8-THC in the amount of about 0.1% to about 90% (wt/wt) of the composition; and at least one emulsifier in an amount of about 0% to about 99.9% (wt/wt) of the composition;

placing the smoke-able composition in an appropriate quantity in an electronic cigarette cartridge;

placing the e-cigarette cartridge containing the smoke-able composition into an electronic cigarette housing; and the mammal smokes the smoke-able composition using the electronic cigarette.

In some embodiments, the smoke-able composition further comprises a flavor enhancer in an amount of about 1% to about 80% (wt/wt) of the composition.

In some embodiments, wherein the flavor enhancer is chosen from a list consisting of apple, cherry, green tea, cinnamon, clove, black tea, plum, mango, dates, watermelon, coconut, pear, jasmine, peach, fennel, fragrant melon, lychee, mint, chocolate, coffee, cream, banana, almond, grape, strawberry, blueberry, blackberry, pine, kiwi, sapote, taro, lotus, pineapple, orange, lemon, melon, peach, licorice, vanilla, rose, Osmanthus, ginseng, spearmint, citrus, cucumber, honeydew, walnut, almond, terpene, and honey.

In another aspect, a system for pulmonary administration of a Δ8-THC composition to a mammal is provided, including:

a cartridge for storing a smoke-able Δ8-THC composition; and an electronic cigarette wherein the cartridge is housed.

In another aspect, a rectal suppository is provided, including Δ8-THC and hemp extracts, wherein the suppository comprises from about 20 mg to about 500 mg of Δ8-THC distillate (70% Δ8-THC) and the oily or fatty base has an ascending melting point between 33 and 35.5° C.

In some embodiments, the oily or fatty base is a hard fat, which can be selected from one or a mixture of the following ingredients: coconut oil, cocoa butter, yellow beeswax, etc.

In another aspect, a powdered Δ8-THC distillate is provided including tea extract powder and Δ8-THC distillate, wherein the Δ8-THC distillate has been absorbed by the tea extract powder.

In some embodiments, the powdered Δ8-THC is further processed into tablet or capsule form. Each tablet or capsule has accurately measured Δ8-THC where 5-50 mg is typical.

In another aspect, beverages containing Δ8-THC distillate are provided, made by mixing the powdered Δ8-THC distillate and other ingredients with water or another suitable beverage base.

In some embodiments, other ingredients can be one or more ingredients, including but not limited to milk, coffee, honey, fruit, alcohol, starch, sugar, lecithin and other commonly used food emulsifiers including MDGs, stearoyl lactylates, sorbitan esters, polyglycerol esters, sucrose esters, etc.

In another aspect, a type of food is provided, wherein one of the ingredients comprises at least 5 mg of Δ8-THC distillate and other ingredients.

In another aspect, a type of beverage is provided, wherein one of the ingredients of the beverage comprises at least 5 mg of Δ8-THC distillate.

In another aspect, a type of food is provided, wherein one of the ingredients includes at least 5 mg of Δ8-THC distillate.

In another aspect, a method to make a smoke-able composition is provided, including steps of:
  adding a quantity of Δ8-THC; and
  transferring heated Δ8-THC and mixing the composition using ultrasound, a propeller, a magnetic stirrer, or a shaking mechanism, wherein the quantity of cannabidiol comprises about 0.1% to about 90% (wt/wt) of the composition.

In some embodiments, the method, further includes the step of adding a quantity of flavor enhancer.

In some embodiments, the method, the quantity of flavor enhancer comprises about 1% to about 80% (wt/wt) of the composition.

In another aspect, a powdered Δ8-THC distillate is prepared by a process including:
  selecting a Δ8-THC distillate with a desired concentration of Δ8-THC;
  measuring a desired quantity of the Δ8-THC distillate;
  selecting a suitable tea extract powder;
  measuring a desired quantity of the tea extract powder to achieve a certain ratio of the tea extract powder to the Δ8-THC distillate by weight; and
  mixing the Δ8-THC distillate and the tea extract powder until the Δ8-THC distillate is evenly absorbed by the tea extract powder.

In another aspect, a method for making tablet pills or powdered Δ8-THC is provided, including:
  selecting a desired concentration of Δ8-THC distillate;
  measuring a desired quantity of the Δ8-THC distillate;
  selecting suitable ingredients and emulsifiers preferable in powder form;
  measuring a desired quantity of the powder ingredients to achieve a certain ratio of powder to Δ8-THC distillate by weight, wherein the ratio of powder to Δ8-THC distillate by weight is 10 g of the powder to every ½ g of Δ8-THC distillate; and
  mixing the powder and Δ8-THC distillate until the Δ8-THC distillate is evenly absorbed by the powder.

In some embodiments, the Δ8-THC distillate can be replaced by hemp extracts containing Δ8-THC and other cannabinoids, including THC, CBD, CBN, CBC, THCV, CBG, etc.

In some embodiments, the powder is tea extract and the ratio of the tea extract powder to the Δ8-THC distillate by weight is between 10 g of tea extract powder for every 0.1-1 g of Δ8-THC distillate.

In some embodiments, the method further includes heating of the Δ8-THC distillate to reduce its viscosity.

In some embodiments, the Δ8-THC distillate is heated to between 80- and 100-degrees Fahrenheit.

In some embodiments, the heating step is continued until the viscosity of the Δ8-THC distillate is substantially close to that of light syrup.

In some embodiments, the heating step includes the heating of a container containing the Δ8-THC distillate using a water bath or via external indirect heating.

In some embodiments, the method further includes: testing the Δ8-THC distillate to determine the concentration of Δ8-THC in the distillate as a percentage by weight; determining the amount of a desired individual dose of Δ8-THC; determining the number of desired individual doses of Δ8-THC in each gram of the desired quantity of Δ8-THC distillate; determining the total number of desired individual doses of Δ8-THC in the powdered Δ8-THC distillate resulting from the mixing step; determining the weight of a powdered Δ8-THC distillate resulting from the mixing step that contains a desired individual dose of Δ8-THC; dividing the powdered Δ8-THC distillate into separate desired individual doses of Δ8-THC based on the weight of the powdered Δ8-THC distillate.

DETAILED DESCRIPTION

Unless defined otherwise, all technical and scientific terms used herein have the same meaning as commonly understood by one of ordinary skill in the art to which the disclosure belongs. Although any methods and materials similar or equivalent to those described herein can be used in the practice or testing of the present disclosure, the preferred methods and materials are described. All publications mentioned hereunder are incorporated herein by reference.

There is a growing base of evidence on the various medicinal benefits of *cannabis*, including its efficacy in the treatment of painful conditions such as migraines, cramps, and convulsions. A 2017 report issued by the National Academy of Sciences, Engineering, and Medicine indicated conclusive or substantial evidence that *cannabis* or cannabinoids are effective for relieving chronic pain in adults, treating chemotherapy-induced nausea and vomiting, and improving patient-reported multiple sclerosis spasticity symptoms. Moreover, the report indicated evidence that *cannabis* or cannabinoids are effective for improving sleep outcomes for patients with obstructive sleep apnea syndrome, fibromyalgia, chronic pain, and multiple sclerosis.

The *cannabis* plant contains many naturally occurring substances that are of great interest in science and medicine. Isolated compounds from the *cannabis* plant include, among others, $\Delta^9$-tetrahydrocannabinol (THC), cannabidiol (CBD), cannabichromene (CBC), cannabigerol (CBG), cannabidivarin (CBDV). While THC has psychoactive effects, CBD, CBC, CBG, and CBDV do not. Isolated compounds from the *cannabis* plant are called cannabinoids. There are a total of eighty-five (85) cannabinoids isolated from the *cannabis* plant.

Many research studies have confirmed the medicinal value of cannabinoids. For instance, cannabinoids have been investigated for possible treatment of seizures, nausea, vomiting, lack of appetite, pain, arthritis, inflammation, and other conditions. $\Delta^9$-tetrahydrocannabinol ($\Delta^9$-THC) is the psychoactive ingredient commonly found in marijuana. The term "industrial hemp" refers to the range of *Cannabis* plants with low $\Delta^9$-THC content. The term "marijuana" refers to the range of *Cannabis* plants with high $\Delta^9$-THC content.

Cannabinoids are a family of compounds that interact with cannabinoid receptors in the human body. $\Delta^9$-THC is one of around 60 cannabinoids present in the *Cannabis sativa* plant. It is the most well-known cannabinoid and is responsible for the characteristic psychoactive effect of *cannabis*. In contrast, $\Delta^8$-THC is an isomer of $\Delta^9$-THC that is less abundant in the *Cannabis* plant and has been studied less extensively in prior research. $\Delta^8$-THC is one of around 60 cannabinoids that naturally occur in the *Cannabis* plant. $\Delta^8$-THC is found in very low concentrations (<0.1%) in CBD hemp flower. It can also be extracted or converted from other cannabinoids and produced in concentrated form for a variety of uses. As compared to $\Delta^9$-THC, $\Delta^8$-THC produces less intense psychometric effects and holds potential to be used in a variety of medical treatments. For instance, research has indicated that $\Delta^8$-THC is 100% more effective than $\Delta^9$-THC in reducing chemotherapy-induced nausea in pediatric cancer patients. Furthermore, the use of $\Delta^8$-THC as an anti-emetic was found to completely prevent vomiting while producing negligible side effects (Abrahamov et al, 1995, Life Sci. 56:2097-2102). In addition, various studies have suggested that $\Delta^8$-THC is an effective therapeutic agent for a range of medical conditions, for instance in reducing pain and inflammation associated with corneal injury and stimulating appetite following weight loss (Avraham et al, 2004, *Pharmacol. Biochem. Behav.* 77:675-684; Thapa et al, 2018, *Cannabis Cannabinoid Res.* 3.1:11-20). Consequently, therapies involving $\Delta^8$-THC and $\Delta^9$-THC hold potential to address a variety of medical conditions and are the subject of further study and implementation.

The IUPAC nomenclature of $\Delta^9$-THC or THC is (−)-(6aR,10aR)-6,6,9-trimethyl-3-pentyl-6a,7,8,10a-tetrahydro-6H-benzo[c]chromen-1-ol. CBD's IUPAC nomenclature is 2-((1S,6S)-3-methyl-6-(prop-1-en-2-yl)cyclo-hex-2-enyl)-5-pentylbenzene-1,3-diol). CBC has the IUPAC nomenclature of 2-methyl-2-(4-methylpent-3-enyl)-7pentyl-5-chromenol. These are among the most prominent compounds in the family of compounds extracted from the *cannabis* plant referred to as cannabinoids.

Cannabinoids can be isolated by extraction from *cannabis* plants. Plants in the *cannabis* genus include *Cannabis sativa*, *Cannabis ruderalis*, and *Cannabis indica*. These plants are the natural sources of cannabinoids. Cannabinoids are also available in synthetic forms. Various methods to synthesize cannabinoids in laboratory settings were discovered and are practiced today. Synthetic cannabinoids are more targeted in that the synthetic compound usually comes isolated without other cannabinoids mixed in.

$\Delta^8$-THC has the IUPAC nomenclature of (−)-(6aR,10aR)-6,6,9-trimethyl-3-pentyl-6a,7,8,10a-tetrahydro-6H-benzo[c]chromen-1-ol. It is rarely extracted directly from plants but can instead be obtained by conversion from THC and/or CBD.

$\Delta^8$-THC is a double-bond isomer of THC and a minor constituent of most varieties of *Cannabis* (Hollister and Gillespie, 1972, *Clin Pharmacol Ther* 14: 353). The main chemical difference between the two compounds is that THC is easily oxidized to cannabinol, whereas $\Delta^8$-THC is not and is in fact very stable. $\Delta^8$-THC, for the most part, produces similar psychometric effects as does $\Delta^9$-THC, but is generally considered to be 50% less potent than $\Delta^9$-THC and has been shown in some cases to be 3-10 times less potent. $\Delta^8$-THC has also been shown to be more (200%) effective as an anti-emetic than $\Delta^9$-THC and has been used as an anti-emetic in children, based on the belief that the side effects of $\Delta^9$-THC and $\Delta^8$-THC, such as anxiety and dysphoria, are more prevalent in adults than children (Abrahamov et al, 1995, *Life Sciences* 56: 20972102). It is also of note that the effect of mixed Cannabinoids (THC and CBD) on $\Delta^8$-THC has not been investigated.

Laboratory-scale methods of converting CBD to $\Delta^8$-THC and $\Delta^9$-THC have been described previously. In one process, CBD was isomerized to $\Delta^8$-THC and $\Delta^9$-THC by boiling a solution of CBD in ethanol containing 0.05% hydrogen chloride for 18 hours, pouring into water, and extracting with ether. The resultant ether solution was washed with water, dried using $Na_2SO_4$, and evaporated. Finally, compounds in the oil obtained, including $\Delta^8$-THC and $\Delta^9$-THC, were isolated by chromatography on alumina (Gaoni and Mechoulam, 1966, *Tetrahedron* 22:1481-1488). The conversion of CBD to $\Delta^9$-THC has also been demonstrated on a laboratory scale by boiling a solution of CBD in 0.05% hydrogen chloride in ethanol for 2 hours and conducting repeated chromatographic separation on alumina (Gaoni and Mechoulam, 1964, *J. Amer. Chem. Soc.* 86:1646). Moreover, G. R. Webster et al. in US patent serial number 20040143126A1 described methods of converting cannabidiol to $\Delta^8$-tetrahydrocannabinol or $\Delta^9$-tetrahydrocannabinol using p-toluenesulfonic acid in toluene. The methods described have been claimed to produce higher yields and higher purity compared to prior art methods. However, these solvent processes require high classification of the facility and are very difficult and expensive to scale up. Conversion processes of CBD to $\Delta^8$-THC and $\Delta^9$-THC without the use of organic solvents have not been previously reported. Eliminating organic solvents in the conversion process provides a safe and economic solution for large-scale production.

With the potential of $\Delta^8$-THC and $\Delta^9$-THC to treat a variety of medical conditions, there is a growing and unfulfilled need for the efficient conversion of CBD to $\Delta^8$-THC or $\Delta^9$-THC in a mass-production setting without the use of solvents. Efficient conversion processes suited to mass production would facilitate the large-scale testing and implementation of $\Delta^8$-THC and $\Delta^9$-THC for medicinal uses and enable further investigation into its properties, medicinal effects, and potential applications.

In patients suffering from Acquired Immune Deficiency Syndrome (AIDS), lack of appetite, nausea, vomiting, and pain are common related symptoms. Cannabinoids are used to treat these conditions. Similarly, symptoms associated with Parkinson's disease, such as tremors, are also treated with cannabinoids. Various conditions may also be treated or alleviated by the absorption of cannabinoids and derivatives thereof. Conditions that may be treated or alleviated include nausea, vomiting, emesis, pain, lethargy, alcohol induced disorders, multiple sclerosis, inflammatory bowel disorders, arthritis, dermatitis, systemic lupus erythematosus, inflammation, convulsions, psychotic episodes, some cancers, peripheral neuropathic pain, diabetic neuropathy, shingles, burns, actinic keratosis, oral cavity sores and ulcers, seborrheic dermatitis, ankylosing spondylitis, Reiter syndrome, psoriatic arthritis, joint pain, chondrocalcinosis, fibromyalgia, musculoskeletal pain, polymyositis, neuropathic-postoperative complications, acute nonspecific tenosynovitis, epicondylitis, bursitis, post-traumatic osteoarthritis, juvenile rheumatoid arthritis, synovitis, pancreatitis, contact dermatitis, bullous dermatitis herpetiformis, eczema, mycosis fungoides, pemphigus, severe erythema multiforme, seborrheic dermatitis, and seizures. Cannabinoids are further shown to have broad antioxidant and neuroprotective properties along with immunomodulatory effects.

When used by humans medicinally or recreationally, *cannabis* can be consumed via a variety of routes, including via vaping or smoking dried flower buds and leaf portions, resins, extracted oils, or waxes. In recent years, many medical patients and recreational users have begun to prefer the consumption of *cannabis* in edible form, for instance by eating lozenges, candies, or baked goods, drinking beverages, or taking tablets or capsules.

As with all concentrated *cannabis* resins, $\Delta^8$-THC distillates are difficult to manage as a culinary ingredient due to their high viscosity. The distillates have the consistency of tree sap in an ambient environment, making them hard to flow and producing a tendency to stick to surfaces. By conversion into powdered form, the distillates can be more easily stored, packaged, and ingested by the consumer. Furthermore, the $\Delta^8$-THC can be more accurately measured and portioned from the master batch into the amount required for a certain application. The powdered form can be adapted to provide greater consistency in portion size when applied to edible and sub-lingual preparations. It can also be more accurately applied to a preparation to obtain a specified volume per portioned batch.

Furthermore, this method would produce an edible powdered $\Delta^8$-THC which allows for faster absorption of cannabinoids into the blood stream than existing ingested edibles. This composition is additionally suitable for use by sub-lingual ingestion.

These and other advantages and features of various embodiments the present disclosure are described with specificity to make the present disclosure understandable to one of ordinary skill in the art.

*Cannabis* abuse among chronic users is also seen, especially when raw *cannabis* plant materials are consumed by smoking. Withdrawal symptoms are observed with discontinuance of *cannabis* use. Collectively, *cannabis* abuse is referred to as *cannabis* use disorder. However, some cannabinoids may be useful in treating *cannabis* use disorder.

Delivering cannabinoids through membranes in mammals remains a challenge. This is due to the hydrophobic nature of cannabinoids. Transdermal delivery of cannabinoids faces many challenges, and penetration enhancers are usually required for effective delivery. Pulmonary delivery has many advantages, one of which is the large available surface area in the pulmonary airways.

$\Delta^8$-THC is generally produced in distillate form and can be vaporized using a standard weed pen or dab rig or mixed with flower to increase its potency level. Since distillate is technically edible, it can be consumed orally. As an emerging trend in *cannabis* consumption, many medical patients and recreational users now prefer to consume *cannabis* by eating or drinking it in edible form, rather than consuming it through smoking or vaping. Due to the solubility characteristics of $\Delta^8$-THC distillate, *cannabis* experts and companies manufacturing oils and drinks containing *cannabis* have encountered significant difficulty in producing an oil that can be added to a drink in a way that the oil will be emulsified, dissolved, or otherwise evenly distributed throughout the drink. In many cases, the $\Delta^8$-THC distillate separates in water-based drinks such as coffee or tea and is thus unpleasant to drink. Moreover, such separation can lead to a medical patient not receiving an accurate dose if the patient does not consume the entire drink, particularly the separated oil portion of the drink. CBD and $\Delta^8$-THC from hemp CBD is marketed in the United States as a dietary supplement. Various products containing hemp extract have been marketed in recent years. Most cannabinoids, including $\Delta^8$-THC, may be consumed by digestion or by transdermal delivery. However, a more effective method to deliver cannabinoids for rapid absorption by a mammal, preferably a human being, has yet to be developed.

Smoking may be necessary in some circumstances. When a person needs a certain substance to be delivered into his/her body, but the substance is only available in smokeable form, that person's options may be limited. An example is the use of medical marijuana. Naturally occurring compounds such as cannabinoids can be found in certain parts of the marijuana plants. A person wishing to consume the compounds found in the marijuana plants due to health reasons and under legal conditions may be limited to smoking the plant materials.

Many people dislike smoking. With the many disadvantages of smoking, such dislikes are justifiably prevalent and understandable. Some simply dislike smoking due to the stigma associated with the habit. To address this problem, vaporizers are used. While eliminating some of the disadvantages of smoking by a cigarette or pipe, vaporizers are bulky, hard to set up, and inconvenient to use.

There is a need to have a means to deliver $\Delta^8$-THC via the pulmonary pathway while ensuring the subject's safety and minimizing risks. Given the benefits of substance delivery via the pulmonary pathway, the disadvantages of smoking, and the available technology of the e-cigarette, this present disclosure offers a method to deliver $\Delta^8$-THC via the pulmonary route while minimizing the adverse effects of smoking.

As used herein, CBD refers to cannabidiol.

As used herein, $\Delta^8$-THC refers to $\Delta^8$-tetrahydrocannabinol.

As used herein, $\Delta^9$-THC refers to $\Delta^9$-tetrahydrocannabinol.

As used herein, "acid" refers to a strong mineral acids such as hydrochloric acid HCl, and/or other natural strong organic acids such as lactic acid, acetic acid, formic acid, citric acid, oxalic acid, malic acid, and tartaric acid.

Described herein are methods and protocols for converting cannabidiol (CBD) to $\Delta^8$-tetrahydrocannabinol ($\Delta^8$-THC) or $\Delta^9$-tetrahydrocannabinol ($\Delta^9$-THC). Changes to the reaction times and temperatures may result in different yields and/or purities of the product. Moreover, where and when appropriate, chemical species may be substituted with their functional equivalents.

Specifically, described herein is a method of converting cannabidiol (CBD) to a $\Delta^8$-THC containing cannabinoids that comprises the following steps: providing a reaction mixture comprising a catalyst without organic solvent, adding CBD isolate or hemp and *cannabis* extracts containing CBD, heating and mixing said reaction mixture, and distilling the cannabinoids from the mixture. The cannabinoids having $\Delta^8$-THC may then be combined with suitable excipients to form a pharmaceutical composition.

In some embodiments, $\Delta^8$-THC at therapeutically effective concentrations or dosages may be combined with a pharmaceutically or pharmacologically acceptable carrier, excipient, or diluent, which can be either biodegradable or non-biodegradable. Possible carriers include but are not limited to poly(ethylene-vinyl acetate), copolymers of lactic acid and glycolic acid, poly(lactic acid), gelatin, collagen matrices, polysaccharides, poly(D,L lactide), poly(malic acid), poly(caprolactone), celluloses, albumin, starch, casein, dextran, polyesters, ethanol, mathacrylate, polyurethane, polyethylene, vinyl polymers, glycols, mixtures thereof and the like. Standard excipients include gelatin, casein, lecithin, gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, polyoxyethylene castor oil derivatives, polyoxyethylene sorbitan fatty acid esters, polyethylene glycols, polyoxyethylene stearates, colloidol silicon dioxide, phosphates, sodium dodecylsulfate, carboxymethylcellulose calcium, carboxymethylcellulose sodium, methylcellulose, hydroxyethylcellulose, hydroxypropylcellulose, hydroxypropylmethycellulose phthalate, noncrystalline cellulose, magnesium aluminum silicate, triethanolamine, polyvinyl alcohol, polyvinylpyrrolidone, sugars and starches.

In these embodiments, the acids may be natural strong organic acids such as lactic acid, acetic acid, formic acid, citric acid, oxalic acid, malic acid, and tartaric acid.

In some embodiments, a base is added to the reaction mixture prior to allowing the reaction mixture to distill. The base may be an alkali metal hydroxide, alkali metal hydrogen carbonate, or alkali metal carbonate.

Purity is determined by analytical HPLC and GC-MS. In GC-MS, the mass of analyte detected in a sample is proportional to its peak area in the total ion chromatogram. If the masses are generally in the same range, the peak areas of individual compounds may be compared with the total peak area of the GC-MS chromatogram. In some embodiments, purity of the $\Delta^8$-THC made from this process can be greater than 80%.

Yield is calculated from the peak area of the isolated compound in the HPLC spectra of the crude reaction product mixture. As sometimes reported, yield is often based on the first isolated crude product before final purification. Yield may range from 50 to 85% in different embodiments of the process.

The following examples describe common uses of the disclosure; however, the disclosure is by no means limited to the examples listed.

Example 1

Conversion of Crude CBD to $\Delta^8$-THC and $\Delta^9$-THC

CBD crude 63% (30 kg) together with oxalic acid catalyst (100 g) was added to the reactor. The mixture was heated slowly under constant stirring at a stable temperature of 90° C. for 2 hours and then 140° C. for 1 hour, although other time periods may also be used as discussed below. 100 g of NaHCO$_3$ was added to the reaction mixture. Finally, the mixture was passed through a wipe film distillation equipment. HPLC on the mixture showed the presence of 44% $\Delta^8$-THC and 17% $\Delta^9$-THC.

In the above example, more than 0.3% oxalic acid is used as catalyst. The exact proportion of the catalyst is not vital to the reaction process. Furthermore, the nitrogen atmosphere does not appear to be as necessary in the conversion of CBD to $\Delta^8$-THC as in the conversion of CBD to $\Delta^9$-THC. It is also of note that no solvents are used in the example above.

The conversion rate and yield of $\Delta^8$-THC may vary based on heating temperature and reaction time.

In other embodiments, another alkali metal hydroxide, alkali metal hydrogen carbonate, or alkali metal carbonate is used instead of NaHCO$_3$.

Example 2

Conversion of CBD Isolate or CBD Concentrate to $\Delta^8$-THC and $\Delta^9$-THC CBD concentrate 80% (30 kg) together with oxalic acid catalyst (100 g) was added to the reactor. The mixture was heated slowly under constant stirring at a stable temperature of 100° C. for 2 hours and then 140° C. for 1 hour, although other time periods may also be used as discussed below. 100 g of NaHCO$_3$ was added to the reaction mixture, which was then passed through a wipe film distillation equipment. HPLC on the mixture showed the presence of 28% $\Delta^8$-THC and 36% $\Delta^9$-THC.

In the example above, more than 0.3% oxalic acid is used as catalyst. The exact proportion of the catalyst is not essential to the reaction process. Furthermore, the nitrogen atmosphere does not appear to be as necessary in the conversion of CBD to $\Delta^8$-THC as in the conversion of CBD to $\Delta^9$-THC. It is also of note that no solvents are used in the example above.

The conversion rate and ratio of $\Delta^8$-THC and $\Delta^9$-THC may vary based on heating temperature and reaction time.

In other embodiments, another alkali metal hydrogen carbonate or alkali metal carbonate is used instead of NaHCO$_3$.

In other embodiments, full conversion from CBD to $\Delta^8$-THC is achieved by adding an additional catalyst consisting of 100 g of oxalic acid and extending heating and stirring for 2 hours before neutralization at 90-100° C. The distilled sample yielded 27 kg of 80% $\Delta^8$-THC without any $\Delta^9$-THC or CBD detected.

While the preferred embodiments of the disclosure have been described above, various modifications may be made therein and the appended claims are intended to cover all such modifications which may fall within the spirit and scope of the disclosure.

$\Delta^8$-THC distillates retain a high viscosity which makes them difficult to manage during food or beverage manufacturing. However, gently warming the oil via water bath transforms the extracted oil into a manageable, low-viscosity liquid. To do this, obtain a vessel large enough to fit the container with the extracted $\Delta^8$-THC distillate and fill it with water. Place the water bath on low heat to slowly and gently warm the water and oil. Slowly and gently heating the oil via a water bath ensures an even application of heat and prevents the oil from burning. Heat the $\Delta^8$-THC distillate until it is approximately the same viscosity as a light syrup or teriyaki sauce. This preferred oil viscosity is achieved at an oil temperature of 80 to 120 degrees Fahrenheit, with the optimal oil viscosity being achieved at an oil temperature about 100 degrees Fahrenheit.

Once the distillate has been gently heated and is at a manageable, liquid viscosity, tea extract or other suitable powder is mixed with the oil using an industrial blender.

Once a manufacturer has determined the weight of tea extract or other powder required to powderize, slowly add the heated oil to the pre-weighed food powder. Mix thoroughly using an industrial blender until the powder is completely uniform. Upon visual inspection, no visible spots of oil and a uniform golden-yellow color should be observed.

From this point, the powder is sent to the lab for testing and dosage corroboration.

Lab tests will aid in honing the exact dosage amounts and should always be deferred to when dosing infused products with a specified amount.

$\Delta^8$-THC powder with 1-10% $\Delta^8$-THC concentration of the present disclosure is used in several exemplar recipes for making edible products and beverages, which are provided below. The examples provided can be safely practiced using home kitchenware. The following examples describe some possible uses of the disclosure; however, the disclosure is by no means limited to the examples listed.

Example 3

$\Delta^8$-THC Milk Tea
Ingredients
  $\Delta^8$-THC powder, tea extracts, creamer, milk protein, sodium polyphosphate, lecithin, mono- and di-glycerides, dipotassium phosphate
Procedure
  Mix well using spray-drying apparatus and package.

Example 4

$\Delta^8$-THC-infused jam
Ingredients
  ¼ cup honey, 4 cups fruit of choice, 2 cups sugar, ¼ cup lemon juice, 20 mg $\Delta^8$-THC powder
Procedure
  Heat sugar and lemon juice in saucepan on low heat. Stir constantly until sugar has dissolved fully. Stir in fruit. Add in $\Delta^8$-THC powder. Heat and stir for roughly 20 minutes. Place ⅛ cup honey at the bottom of each jar. Divide the contents of the saucepan evenly between each mason jar. Stir thoroughly to evenly distribute the honey. Allow contents to cool before serving.

Example 5

Hot Chocolate Mix
Ingredients
  1½ cups (7½ oz/212 g) dry milk powder, ½ cup (4 oz/115 g) sugar, ½ cup (2 oz/57 g) unsweetened cocoa powder, 2 teaspoons corn starch, 100 mg $\Delta^8$-THC powder
Procedure
  Sieve all the ingredients into a bowl and keep in an air-tight container.
  To make a mug of hot chocolate,
  a) Add three tablespoons of the hot chocolate mix to 8 oz milk or water in a saucepan and stir until homogenized Simmer on medium/low heat for two minutes.
  b) Pour into mug and serve with marshmallows or another preferred topping.

Example 6

Instant Oatmeal
Ingredients
  1 pkg. (1.5 oz) instant oatmeal, ⅔ cup water or milk, 1 g $\Delta^8$-THC powder
Procedure
  Empty contents of package into a microwave-safe bowl. Add THC powder to dry oats. Add ⅔ cup water or milk and stir. Microwave as directed. Remove from microwave and stir thoroughly before serving.

Example 7

Beverages (water, lemonade, tea, coffee, hot cocoa, soda, juice, milk, cider, bouillon (broth), shakes and smoothies, etc.)
Ingredients
  10 mg $\Delta^8$-THC powder, beverage of choice
Procedure
  Mix/dissolve $\Delta^8$-THC powder into hot water or beverage.
  $\Delta^8$-THC powder can be added in the same manner as any other ingredient when blending a milkshake or fruit smoothie without the application of heat. As easily inferred, the application of heat to a shake or smoothie would deteriorate the quality of such beverages. Adding the $\Delta^8$-THC powder during the blending process lends itself well to making infused shakes/smoothies without heat and does not produce issues like clumping or sticking of oil onto the sides of the container if sufficient blending, i.e., for at least 2-3 minutes, is carried out.

Preparation of Suppositories
Suppositories may be prepared via the following procedure:
  a) Add 0.6 kg of $\Delta^8$-THC distillate, 4 kg of hard butter, 4 kg yellow beeswax, and 2 kg of coconut oil to a mix tank.
  b) Begin heating the batch to 60° C. by recirculating steam through the tank jacket.
  c) Begin mixing with the sweeps at 12 Hz as the product begins to melt. Continue heating to a target temperature of 60° C. Mix until the product is completely molten, increasing the sweeps to 60 Hz as the product melts. Mix for a minimum of 30 minutes, maintaining the temperature at 58-62° C. using the hot box (target temperature=60° C.).
  d) During the mixing period, flush the product through the bottom valve using a large pot. Continue flushing throughout the mixing interval until product appears visually uniform. Return the product to the mix tank.
  e) Fill each mold. Remove one suppository per filling head. Fill weights of individual suppositories should be between 2.85 and 3.15 g.

This present disclosure also relates to a composition comprising $\Delta^8$-THC with emulsifiers and/or flavor enhancers. The resulting composition may be vaporized by the heat applied by an electronic cigarette. A mammal, preferably a human, may inhale this vapor, which contains $\Delta^8$-THC. Upon inhalation, the mammal may absorb the $\Delta^8$-THC via the pulmonary route.

In a preferred embodiment, $\Delta^8$-THC is naturally derived and provided as a part of hemp extract. Impurities may be any cannabinoids that are not $\Delta^8$-THC, fatty acids such as linoleic acid and α-linoleic acid, which are natural components of hemp extracts, β-caryophyllene, myrcene, and β-sitosterol.

In another preferred embodiment, $\Delta^8$-THC may be artificially synthesized and is substantially free from impurities. Synthetic $\Delta^8$-THC can be vaporized as well.

According to the present disclosure, the composition can be pure $\Delta^8$-THC or a mixture with an emulsifier, preferably polyethylene glycol 400 (PEG-400), but may also be propylene glycol or vegetable glycol. PEG-400 is highly hydrophilic. The combination of $\Delta^8$-THC in hemp oil and PEG-400 gives in a uniform composition. Moreover, this composition does not separate, ensuring even distribution of $\Delta^8$-tetrahydrocannabinol in the composition.

Vegetable glycol gives more smoke when the composition vaporizes during use while propylene glycol enhances the taste of the composition during vaporization. The weight percentage of propylene glycol or vegetable glycol in the composition is the same as that recommended for the polyethylene glycol-400 concentration.

In another embodiment, a combination of different emulsifiers may be used. Using a combination of PEG-400 and vegetable glycol gives the composition a smoother feel, produces more smoke with each drag, while guarding against separation when the composition is left unused for extended periods.

$\Delta^8$-THC is the main component to be delivered in this composition. In this composition, $\Delta^8$-THC concentration is present in a total amount by weight of about 0.1% to about 99%.

In another preferred embodiment, $\Delta^8$-THC may be present in an amount of about 50% to about 80% (wt/wt) of the composition.

The emulsifier is present in this composition in a total amount by weight of about 10% to about 99.9%.

When PEG-400 and vegetable glycol are used together, PEG-400 comprises most of the emulsifier mass. Specifically, PEG-400 may be present by weight at between about 40% to about 80%, and vegetable glycol may be present by weight at between about 5% to about 15%. The balance of the composition may be flavor enhancer and $\Delta^8$-THC.

The composition may further comprise a flavor enhancer to substantially change the flavor of the smoke. The flavor enhancer is present in this composition in a total amount by weight of about 1% to about 80%.

In a preferred embodiment, the flavor enhancer is present in the amount by weight of about 20% to about 40% of the composition. In yet another preferred embodiment, the flavor enhancer is present in the amount by weight of about 40% to about 60% of the composition. In another embodiment, different kinds of flavor enhancer may be mixed in such that the smoke-able composition may have multiple flavors.

In another preferred embodiment, $\Delta^8$-THC may be mixed with a flavor enhancer and without an emulsifier. Trace amount of water and other impurities may be present. In this embodiment, $\Delta^8$-THC may be supplied in less pure form, wherein the $\Delta^8$-THC is in oil form with other cannabinoids and other components of hemp oil, such as linoleic acid, $\alpha$-linoleic acid, $\beta$-caryophyllene, myrcene, and $\beta$-sitosterol. THC may be present in trace amounts. Impurities may be present in the amount of less than 1%.

$\Delta^8$-THC and a flavor enhancer may be obtained in a desired quantity. The two components are placed in a container and mixed using a propeller, a magnetic stirrer or a shaking mechanism. Magnetic stirrer is the best mixing method, as it prevents minor bubbles from forming in the mixture and affecting the smoking experience. After mixing, the composition may be used for smoking.

In this embodiment, $\Delta^8$-THC is present in a total amount by weight of about 70% to about 95%.

A flavor enhancer is present in a total amount by weight of about 5% to about 50%.

Polyethylene glycol-400 (PEG-400), propylene glycol, and vegetable glycol are widely available from industrial sellers and the marketplace. PEG-400 is the most effective emulsifier, as it has strong hydrophilic capability, even though propylene glycol and vegetable glycol are also effective.

$\Delta^8$-THC is made from CBD and/or THC extracted from the *cannabis* plant, namely from industrial hemp, and may be obtained on the legal market. $\Delta^8$-THC may also be obtained from synthetic sources.

Flavor enhancers may be chosen from the list comprising of apple, cherry, green tea, cinnamon, clove, black tea, plum, mango, date, watermelon, coconut, pear, jasmine, peach, fennel, fragrant melon, lychee, mint, chocolate, coffee, cream, banana, almond, grape, strawberry, blueberry, blackberry, pine, kiwi, sapote, taro, lotus, pineapple, orange, lemon, melon, peach, licorice, vanilla, rose, Osmanthus, kiwi, ginseng, spearmint, citrus, cucumber, honeydew, walnut, almond, honey, or any other flavor. Flavor enhancers are available for purchase commercially. Most flavor enhancers are available in oil form and mix well with $\Delta^8$-THC and emulsifiers.

Polyethylene glycol (or vegetable glycol, or propylene glycol) may be combined with $\Delta^8$-THC and a flavor enhancer. The resulting mixture is stirred or mixed well by a propeller, magnetic stirrer, ultrasound or shaking mechanism.

In a preferred embodiment, $\Delta^8$-THC is present at a concentration of about 50% (wt/wt). A flavor enhancer, such as mint, is present at a concentration of about 5% (wt/wt). Trace amounts of water may be found in this composition. $\Delta^8$-THC vaporizes well during smoking by an e-cigarette.

Flavor enhancers may be added into the mixture as needed. The weight percentages for flavor enhancers are given above.

Trace amount of water and other cannabinoids may be present in this composition, as the $\Delta^8$-THC purification process may leave trace amounts of other cannabinoids. It is to be understood that $\Delta^8$-THC may contain certain impurities.

The smoke-able $\Delta^8$-THC composition may be smoked using an e-cigarette. The composition may be injected into an e-cigarette cartridge. The e-cigarette cartridge containing the smoke-able composition may be placed into an e-cigarette housing and be ready for smoking. The e-cigarette may be charged before the smoking of the smoke-able $\Delta^8$-THC composition. Upon inhalation of the smoke from the smoke-able $\Delta^8$-THC composition, $\Delta^8$-THC is delivered into the pulmonary pathway and absorbed by the smoker.

In the following examples, $\Delta^8$-THC is provided as part of hemp oil. Hemp oil in the following examples contains 50% (wt/wt) of $\Delta^8$-THC. Hence, 1 g of hemp oil contains 0.5 g of $\Delta^8$-THC.

Example 8

TABLE 1

Δ⁸-THC e-cigarette liquid

| Ingredient | Weight (g) | % w/w |
|---|---|---|
| Δ⁸-THC (in hemp oil) | 99 | 99 |
| Mint oil | 1 | 1 |
| Total | 100 | 100 |

All ingredients are obtained in the specified quantity above. Weigh 99 g of Δ⁸-THC into a container. Heat the container to a maximum of 80° C. Use a pipette to transfer small amounts of liquid. Finally, mix 1 g mint flavor thoroughly with Δ⁸-THC in the container.

Example 9

TABLE 2

Δ⁸-THC e-cigarette liquid composition with vegetable glycol

| Ingredient | Weight (g) | % w/w |
|---|---|---|
| Vegetable glycol | 80 | 80 |
| Δ⁸-THC (in hemp oil) | 14 | 14 |
| Orange oil | 6 | 6 |
| Total | 100 | 100 |

All ingredients are obtained in the specified quantity above. Weigh 80 g of vegetable glycol and 14 g of Δ⁸-THC into a container. Heat the container to a maximum of 80° C. Use a pipette to transfer small amounts of liquid. Weigh 6 g of orange oil and mix thoroughly with vegetable glycol and Δ⁸-THC before use.

Example 10

TABLE 3

Δ⁸-THC e-cigarette liquid composition with PEG-400 and strawberry flavor

| Ingredient | Weight (g) | % w/w |
|---|---|---|
| Propylene glycol 400 (PEG-400) | 69 | 69 |
| Δ⁸-THC (in hemp oil) | 1 | 1 |
| Strawberry flavor | 30 | 30 |
| Total | 100 | 100 |

All ingredients are obtained in the specified quantity above. Weigh 69 g of PEG-400 into a container. Use a pipette to transfer small amounts of liquid. Weigh 1 g of Δ⁸-THC, then mix with PEG-400 in the container. Add 30 grams of strawberry flavor into the container. Mix the ingredients thoroughly before use.

All references, including publications, patent applications, and patents cited herein, are hereby incorporated by reference to the same extent as if each reference were individually and specifically indicated to be incorporated by reference and were set forth in its entirety herein.

It will be readily apparent to those skilled in the art that various modifications and changes may be made without departing from the spirit and the scope of the present disclosure. Any ranges, ratios, and range of ratios that can be derived from the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art will appreciate that such values are unambiguously derivative from the data presented herein.

Although specific embodiments of the disclosure have been disclosed, those having ordinary skill in the art will understand that changes can be made to the specific embodiments without departing from the spirit and scope of the disclosure. The scope of the disclosure is not to be restricted, therefore, to the embodiments disclosed.

What is claimed is:

1. A method of converting cannabidiol and/or Δ9-tetrahydrocannabinol into Δ8-tetrahydrocannabinol consisting essentially of:
   a) providing a reaction mixture consisting essentially of catalysts; and cannabidiol and/or Δ9-tetrahydrocannabinol without using an organic solvent;
   b) stirring and heating said reaction mixture in a reactor and a water tank at 90° C.-160° C. for 1-10 hours connected by a tube or pipe with one side immersed in water;
   c) adding additional catalysts and extending the reaction time;
   d) cooling the reaction mixture down to room temperature and repeating the above steps by adding additional catalysts and heat;
   e) neutralizing said reaction mixture with a neutralization agent selected from the group consisting of NaOH, KOH, NaHCO3 and Na2CO3;
   f) distilling the reaction mixture with molecular wipe film distillation under vacuum to yield a Δ8-tetrahydrocannabinol distillate;
   g) heating of the Δ8-tetrahydrocannabinol distillate to reduce its viscosity, wherein the Δ8-tetrahydrocannabinol distillate is heated to between 80° F.- and 100° F., the heating step is continued until the viscosity of the Δ8-tetrahydrocannabinol distillate is substantially close to that of light syrup; and the heating step comprises the heating of a container containing the Δ8-tetrahydrocannabinol distillate using a water bath or via external indirect heating;
   h) testing the Δ8-tetrahydrocannabinol distillate to determine the concentration of Δ8-tetrahydrocannabinol in the distillate as a percentage by weight;
   i) determining the amount of a desired individual dose of Δ8-tetrahydrocannabinol;
   k) determining the number of desired individual doses of Δ8-tetrahydrocannabinol in each gram of the desired quantity of Δ8-tetrahydrocannabinol distillate;
   l) determining the total number of desired individual doses of Δ8-tetrahydrocannabinol in the powdered Δ8-tetrahydrocannabinol distillate resulting from the mixing step;
   m) determining the weight of the powdered Δ8-tetrahydrocannabinol distillate resulting from the mixing step that contains a desired individual dose of Δ8-tetrahydrocannabinol; and n) dividing the powdered Δ8-tetrahydrocannabinol distillate into separate desired individual doses of Δ8-tetrahydrocannabinol based on the weight of the powdered Δ8-tetrahydrocannabinol distillate.

* * * * *